United States Patent [19]
Hersh et al.

[11] Patent Number: 5,200,426
[45] Date of Patent: Apr. 6, 1993

[54] INHIBITORS OF NEUTRAL ENDOPEPTIDASE/CALLA AS CHEMOTHERAPEUTIC AGENTS

[75] Inventors: Louis B. Hersh, Dallas, Tex.; R. C. Bateman, Jr., Hattiesburg, Miss.

[73] Assignee: Board of Regents, The University of Texas, Austin, Tex.

[21] Appl. No.: 567,499

[22] Filed: Aug. 14, 1990

[51] Int. Cl.$^5$ .................. A61K 31/335; C07C 255/19; C07C 229/24

[52] U.S. Cl. .................................. 514/475; 514/563; 514/564; 514/565; 558/405; 549/551; 562/444; 562/448; 562/564; 562/567; 562/568; 562/576; 562/571

[58] Field of Search .............. 562/444, 448, 564, 567, 562/576; 549/551; 514/475, 564, 565, 563

[56] References Cited

PUBLICATIONS

Shipp et al., "Molecular Cloning of the Common Acute Lymphoblastic Leukemia Antigen (CALLA) Identifies a Type II Integral Membrane Protein", *Proc. Natl. Acad. Sci.*, 1988 vol. 85, pp. 4819-4823.

Letarie et al., "Common Acute Lymphocytic Leukemia Antigen is Identical to Neutral Endopeptidase", *J. Exp. Med.*, 1988, vol. 168, pp. 1247-1253.

Erdos et al., "Neutral Endopeptidase 24.11 (Enkephalinase) and Related Regulators of Peptide Hormones", *FASEB J.*, 1989, vol. 3, pp. 145-151.

Carrel et al., "Expression of HLA-DR and Common Acute Lymphoblastic Leukemia Antigens on Glioma Cells", *European Journal of Immunology*, 1982, vol. 12, pp. 354-357.

Murthy et al., "Inhibitors of an Enkephalin Degrading Membrane-Bound Metalloendopeptidase: Analgesic Properties and Effects on Striatal Enkephalin Levels", *European Journal of Pharmacology*, 1984, vol. 102, pp. 305-313.

Maldonado, et al., "Differences in Physical Dependence Induced by Selective $\mu$ or $\delta$ Opioid Agonists and by Endogenous Enkephalins Protected by Endogenous Enkephalins Protected by Peptidase Inhibitors", *Brain Research*, 1990, vol. 520, pp. 247-254.

Al-Rodhan et al., "The Antinociceptive Effects of SCH-32615, a Neutral Endopeptidase (Enkephalinase) Inhibitor, Microinjected into the Periagueductal, Ventral Medulla and Amygdala", *Brain Research*, 1990, vol. 520, pp. 123-130.

Shipp et al., "Common Acute Lymphoblastic Leukemia Antigen (CALLA) is Active Neutral Endopeptidase 24.11 (Enkephalinase): Direct Evidence by cDNA Transfection Analysis", *Proc. Nat. Acad. Sci.*, 1989, vol. 86, pp. 297-301.

Bateman, Jr. et al., "N-Bromoacetyl-D-Leucylglycine", *Journal of Biological Chemistry*, 1990, vol. 265, pp. 8365-8368.

Bateman, Jr. et al., "Evidence for an Essential Histidine in Neutral Endopeptidase 24.11", *Biochemistry*, 1987, vol. 26, pp. 4237-4242.

Primary Examiner—Alan L. Rotman
Assistant Examiner—A. A. Owens
Attorney, Agent, or Firm—Arnold, White & Durkee

[57] ABSTRACT

The present disclosure relates to inhibitors of neutral endopeptidase (NEP) which are proposed as novel agents for the treatment of CALLA+ positive cancers as well as other conditions such as hypertension.

35 Claims, 6 Drawing Sheets

Compound I

BADLG

Compound IIa,b

R = H- (a), BrCH$_2$- (b)

Compound III

Compound IV

Compound V

Compound VI

INHIBITORS OF NEUTRAL ENDOPEPTIDASE/CALLA AS CHEMOTHERAPEUTIC AGENTS

The United States Government may own certain rights in the present invention pursuant to NIDA grants 02243 and 05308.

BACKGROUND OF THE INVENTION

1. Field of the Invention

The present invention relates to methods of inhibiting the metallopeptidase, neutral endopeptidase (NEP), which is also referred to as neutral endopeptidase 24.11, CALLA, enkephalinase, enkephalinase A, common acute lymphoblastic leukemia antigen (CALLA) and atriopeptidase. Included are methods for treating acute lymphoblastic leukemia and other CALLA-positive (CALLA+) tumors in mammals, particularly in man. In particular aspects, the invention relates to the identification and selection of NEP inhibitors which are proposed to be useful in treatment of common acute lymphoblastic leukemia, CALLA+ gliomas, certain hepatomas, and hypertension.

2. Description of the Related Art

In mammals, NEP is found in a variety of tissues, including kidney, lung, testes, and brain. Because NEP's biological function can vary from tissue to tissue, it has become known under various names: neutral endopeptidase 24.11, enkephalinase, enkephalinase A, common acute lymphoblastic leukemia antigen (CALLA) and atriopeptidase. Thus the terms NEP, CALLA, and enkephalinase may be used interchangeably to refer to the same protein. NEP is a zinc-containing metallopeptidase. It also is an integral membrane glycoprotein whose structure is thought to be comprised of a twenty amino acid cytoplasmic domain, a single twenty-three amino acid membrane spanning domain, and a 699 amino acid extra-cellular domain, which includes the active site of the enzyme. NEP cleaves peptides on the amino side of hydrophobic amino acids. NEP's known biologically active peptide substrates include Met-Enkephalin, Leu-Enkephalin, ANF, substance P, angiotensin I, II, and III, LHRH, neurotensin, β-lipotropin, oxytocin, fMet-Leu-Phe, neurokinin A, somatostatin, neurokin B, gastrin, bradykinin, gamma-endorphin, Met-Enk-Arg-Phe, CCK-8, Dynorphin-13, Dynorphin-9, Physalaemin, endothelins 1, 2, and 3, and bombesin and its related peptides.

It has been discovered that NEP is identical to an antigen known as common acute lymphoblastic leukemia antigen (CALLA or CD10). CALLA is found on pre B-cell leukemias (49). On mature B-cells CALLA is barely detectable. It is believed that CALLA plays a role in pre B-cell growth and/or differentiation. Through polyclonal and monoclonal antibody techniques, CALLA has been found on the majority of non-T, non-B acute lymphoblastic leukemia cells (48), a large percentage (40%) of chronic myelogenous leukemias in blast crisis (48), on tumor cells from nodular poorly differentiated lymphomas and Burkitt's lymphoma (51) and on myeloma tumor cells (52). The antigen appears absent from acute Myelogenous leukemias and mature B- and T- cell lymphomas (51). CALLA has been detected on early lymphoid progenitor cells and mature granulocyte and fibroblasts (53-55). This antigen has been used in the diagnosis and therapy of lymphoid malignancies (57-59).

The majority of research conducted on NEP has been on its role in pain receptors. The object of such research has been to develop reversible inhibitors as analgesics (see e.g., ref. 34). There is also current interest in reversible NEP inhibitors as antihypertensives. Because of their focus on reversible inhibitors, little effort has been put into finding irreversible inhibitors to NEP. In fact only recently has a mechanism based irreversible inhibitor of a metallopeptidase been published (15).

SUMMARY OF THE INVENTION

The present invention is based on the surprising discovery that reversible NEP inhibitors exhibit a significant inhibitory effect on the growth of CALLA+ leukemia cells. Based on these observations, the inventors contemplate that compounds with NEP inhibitory activity will be effective chemotherapeutic agents against CALLA+ cancers and tumors found in mammals, including humans, particularly when the cancer or tumor is a common acute lymphoblastic leukemia.

Accordingly, it is an object of this invention to provide chemotherapeutic agents for treating acute lymphoblastic leukemia and other CALLA+ tumors. It is a particular object of this invention to provide for such uses high affinity irreversible inhibitors of NEP which may be used both in clinical treatment protocols, as well as to study the enzyme's involvement in B-cell development and differentiation.

The compound Bromoacetyl-D-Leu-Gly (BADLG) is one such compound that irreversibly inhibits NEP, apparently through interaction of BADLG's bromoacetyl moiety with a histidine residue in the enzyme's active site. It is proposed that the binding affinity of BADLG for the active site can be increased by substituting various hydrophobic amino acids for D-Leu, including D-valine and D-isoleucine. Other modifications include substituting alanine or beta-alanine for BADLG's glycine, or rendering a hydrophobic amino acid inactive by modification to the alpha-nitrogen. An example of this inhibitor is bromoacetyl(N-methyl)-Leu-(or Phe)-Ala.

Similarly, it is proposed that analogs of bromoacetyl-(N-hydroxyl)Leu(or Phe)-Ala, will react by means of the bromoacetyl group with nucleophilic residues at NEP's active site:

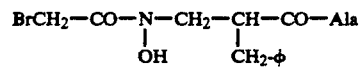

Modifications to the inhibitor include substituting an isobutyl group for the benzyl group.

Inactivated N-acyl substrate analogs are expected to have a different stereochemical conformation, or formation in the active site of NEP than the parent compound, BADLG, and thus may react with different active site residues than the parent compound. An example of an inactivated N-acyl substrate analog to which modifications can be made is:

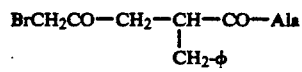

Modifications to increase the affinity of this inhibitor include placing bulky substituents, such as benzyl groups, isopropyl groups naphthyl groups, and the like, at the methylene carbon. Metal chelating groups such as the carboxymethyl group should also increase the affinity of the inhibitor for the enzyme. An example of such a compound is:

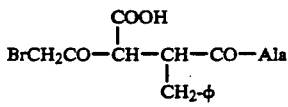

Other contemplated inhibitors are acetylene or nitrile substrate analogs, an example of which is a compound with the formula:

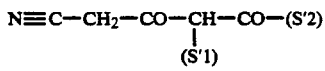

Wherein S'1 is a benzyl or isobutyl group, or analogs thereof, and S'2 is alanine, or beta-alanine. A particular example of this type of compound is:

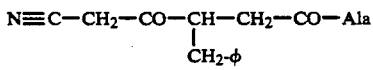

It is believed that acetylene or nitrile substrate analogs will act against metallopeptidases such as NEP by conversion of the acetylene or nitrile derivatives into reactive allenes or ketenimines upon NEP's abstraction of the neighboring methylene hydrogen.

Another proposed group of inhibitors are the diazoketone containing inhibitors that have a diazoketone group within reactive proximity to residues participating in enzyme catalysis. A general example of such a diazoketone containing substrate analog is:

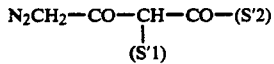

A specific example of this type of compound is:

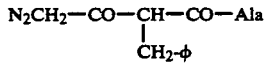

Still another type of inhibitor is a substrate analog containing an appropriately positioned epoxide group, which upon protonation, could react with nucleophilic residues in the active site. An example of this type of compound is:

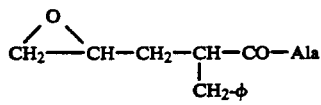

Subjecting CALLA+ tumors to effective amounts of any one of these inhibitors is expected to inhibit the growth and differentiation of the tumor cells. It is further expected that cell death will ultimately result from treatment with such an inhibitor. Irreversible inhibitors will prove particularly useful, and should prevent residual enzymatic activity. For these and other reasons, irreversible inhibitors will be preferred over reversible inhibitors for treating CALLA+ cancers and tumors.

DETAILED DESCRIPTION OF THE PREFERRED EMBODIMENTS

Introduction

Figure 1A:
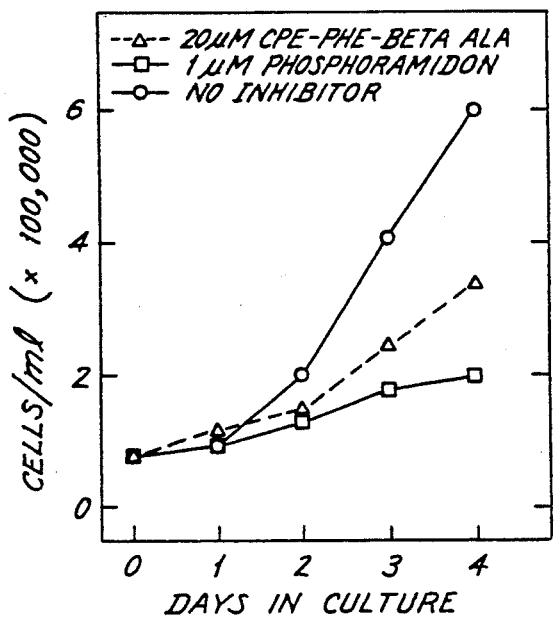
FIG. 1—Effect of NEP Inhibitors on the Growth of Nalm-6, A2/3, and J558 Cell Lines. The two NEP inhibitors phosphoramidon (1 $\mu M$) and carboxyphenylethyl-Phe-$\beta$-Ala (20 $\mu M$) were added to cells plated in quadruplicate at a density of 100,000 cells/ml in 24 well microtiter plates. The number of viable cells was determined daily.

Neutral endopeptidase 24.11 (NEP) cleaves peptides on the amino side of hydrophobic amino acids. The enzyme was originally described by Kerr and Kenny in 1974 (26) as a component of kidney microvillar membranes. NEP was purified using the $\beta$-chain of insulin as a substrate and characterized in terms of its physical properties (27). The enzyme is an integral membrane glycoprotein containing a 20 to 27 amino acid cytoplasmic domain, a single 23 amino acid membrane spanning domain, and a 699 amino acid extracellular domain which includes the active site of the enzyme. Shortly after the description of NEP the enzyme more or less joined the ranks of obscurity until 1978 when two groups (28, 29) reported the finding of a peptidase in rat brain which cleaved enkephalins at the Gly-Phe bond. This enzyme, which was named enkephalinase (28), was proposed to function by degrading endogenously released enkephalins at enkephalinergic synapses terminating their action. This sytem was presumed to be analogous to the regulation of acetylcholine levels at cholinergic synapses by acetylcholinesterase (30). This concept is supported by studies which demonstrate that inhibition of enkephalinase produces analgesia in experimental animals (31-35).

Since enkephalinase activity released a dipeptide from the C-terminus of enkephalins, it was initially classified as a dipeptidyl carboxypeptidase (36) similar in action to angiotensin converting enzyme. However, a number of laboratories have recognized that the enzyme was actually an endopeptidase (32, 33, 37-39) From this observation followed the realization that enkephalinase is the neutral endopeptidase described by Kerr and Kenny. It soon became appreciated that this endopeptidase is found in a variety of tissues including kidney, lung, testis, and brain; with kidney having the highest levels and brain one of the lowest levels (40, 41). It also became apparent that there are numerous physiologically active peptides which can be considered as potential in vivo substrates of the enzyme. A partial list, shown in Table 1 below, includes over 20 physiologically active peptides. The enzyme is the most active peptidase which acts on substance P (42), and is likely the enzyme responsible for regulating atrial naturitic peptide (ANF) (43) and endothelin levels.

TABLE 1

Biologically Active Peptide Substrates For Neutral Endopeptidase 24.11

| | | |
|---|---|---|
| Met-Enkephalin | Neurotensin | Bradykinin |
| Leu-Enkephalin | β-lipotropin | c-endorphin |
| ANF | Oxytocin | Met—Enk—Arg—Phe |
| Substance P | fMet—Leu—Phe | CCK-8 |
| Angiotensin I | Neurokinin A | Dynorphin-13 |
| Angiotensin II | Somatostatin | Dynorphin-9 |
| Angiotensin III | Neurokinin B | Physalaemin |
| LHRH | Gastrin | Endothelins |

In a totally separate research area, efforts to identify cell surface antigens which could serve as markers for human leukemias led to the generation of several polyclonal (44-47) and monoclonal antibodies (48-50) directed against an epitope referred to as the common acute lymphoblastic leukemia antigen or CALLA. This protein was found on the majority of non-T, non-B acute lymphoblastic leukemia cells (48), on a large percentage (40%) of chronic myelogenous leukemias in blast crisis (48), on tumor cells from nodular poorly differentiated lymphomas and Burkitt's lymphoma (51) and on myeloma tumor cells (52). The antigen appears absent from acute myelogeous leukemias and mature B- and T-cell lymphomas (51). CALLA has been detected on early lymphoid progenitor cells (53-55) and mature granulocytes and fibroblasts (56). This antigen has been used in the diagnosis and therapy of lymphoid malignancies (57-59).

Cloning of the cDNA for the enzyme NEP (60-62) and for the antigen CALLA (63) were performed independently. Several months after the publication of the sequence of the cDNAs it was recognized that NEP and CALLA were one and the same (1,64). This interesting finding raises a number of intriguing questions regarding the possible function of this enzyme in B cell development and the substrates for the enzyme which might be involved in this process. Moreover, there are a number of reversible inhibitors of the neutral endopeptidase which are currently being examined clinically as analgesic agents (33, 34).

Various studies of one of the inventors have focused on enkephalin metabolism with emphasis on the enzymes NEP (enkephalinase, CALLA) and enkephalin degrading aminopeptidases. In connection with this work, NEP has been purified from rat brain (65), human kidney (66), and rat kidney (11) and the enzyme has been characterized in terms of its physical properties and substrate specificity. It has further been shown that several opioid peptides other than the enkephalins are substrates (68), as well as non-opioid peptides such as bradykinin and angiotensin (66). In addition a series of synthetic fluorogenic substrates containing blocked N-terminal and C-terminal amino acids were used as substrates for the enzyme (67,69,70). These studies as well as those of others (37, 69-72), served to define the enzyme as a neutral endopeptidase apparently identical to the neutral endopeptidase first described by Kerr and Kenny (26, 27).

Studies by the inventors on the identification of active site residues involved in catalysis have made use of the reagent diethylpyrocarbonate to establish the involvement of an active site histidine serving as an acid-base catalyst (18). The involvement of this and perhaps a second histidine in catalysis came from kinetic studies using N-acyl dipeptides as substrates and inhibitors. Based in part on these and other studies, the inventors have synthesized N-bromoacetyl-D-Leu-Gly as the first active site directed irreversible inhibitor of the enzyme. This compound acts as a competitive inhibitor (Ki=5 mM) as well as an irreversible inhibitor with 1 mol incorporated per mol of enzyme. A single modified histidine residue, histidine 704, was identified. Moreover, an Arg to Gln mutant was used to establish the role of an active site arginine in catalysis (4). Based on modeling studies (74) a putative active site Val involved in substrate binding was identified. The kinetic properties of a Val to Leu mutant are consistent with this residue being involved in substrate binding.

Figure 1B:
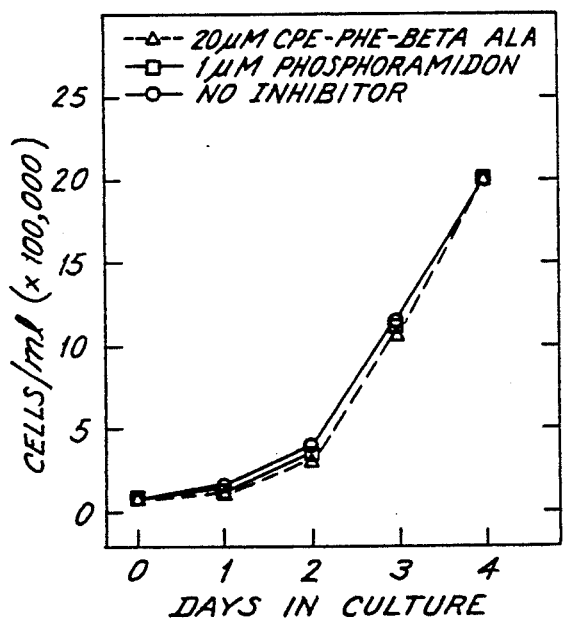
Figure 1C:
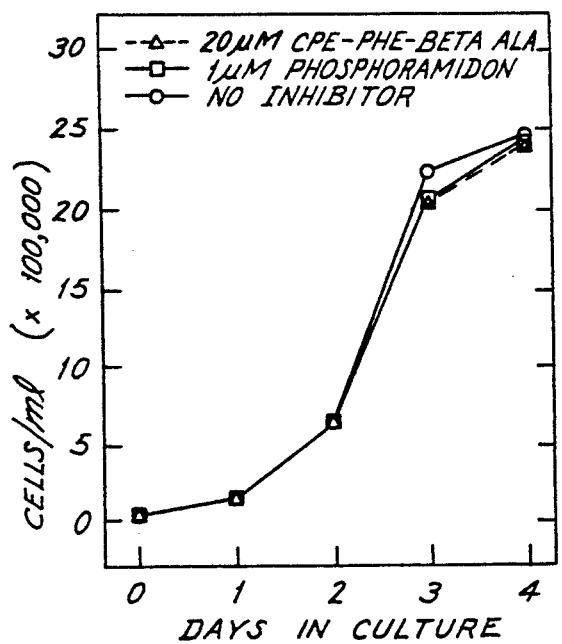
Figure 2A:
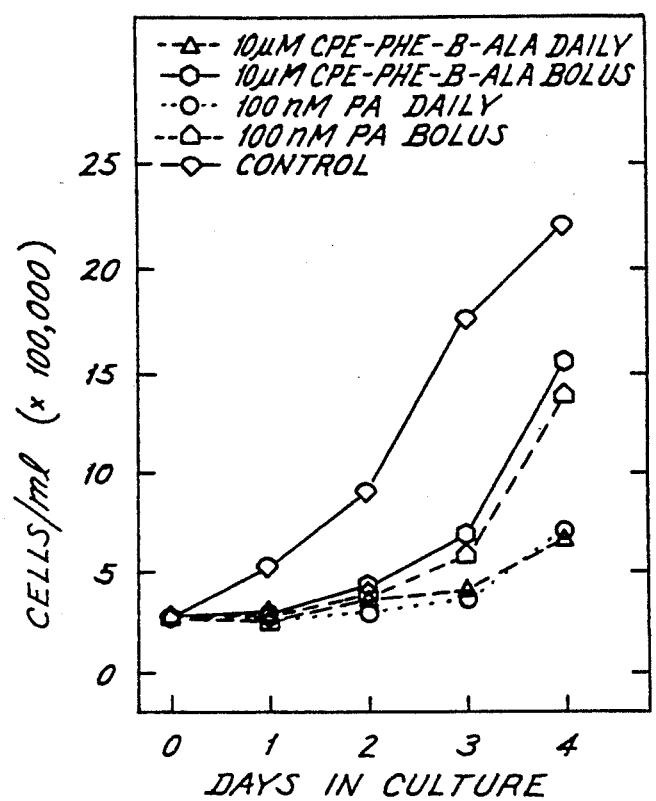
FIG. 2—Effect of NEP Inhibitors on the Growth of Nall-1 and SMS-SB Cell Lines. The NEP inhibitors phosphoramidon (10 nM) and carboxyphenylethyl-Phe-$\beta$-Ala(10 $\mu M$) were added to cells plated at a density of 200,000 cells/ml. The inhibitors were added either once on Day 0 as a bolus (closed circle and square) or daily (open circle or triangle). The number of viable cells was determined daily.
Figure 2B:
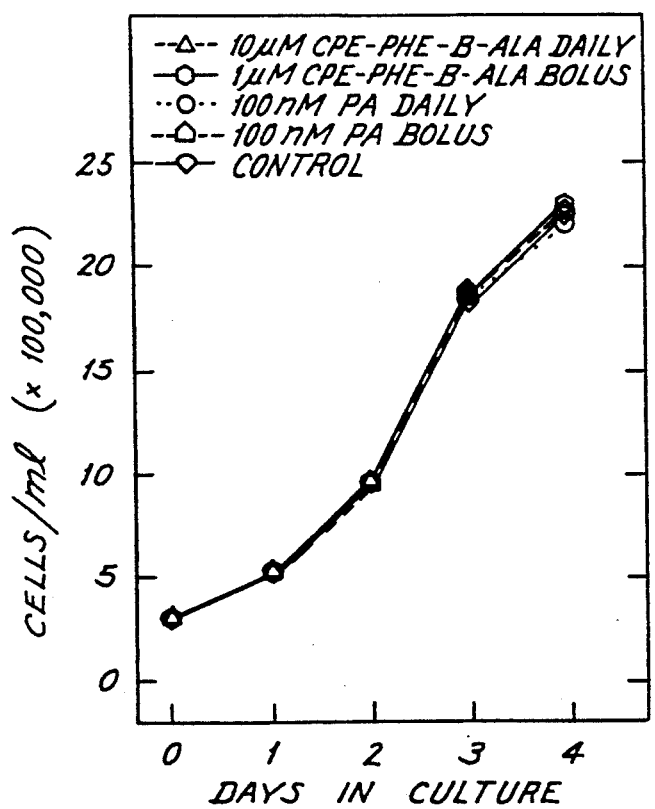

In collaboration with others, the present inventors have demonstrated that neutral endopeptidase 24.11 ("enkephalinase") and CALLA are the same protein (1). Using CALLA+ leukemia cell lines Nalm-6 (75) and Nall-1 (76) the inventors have observed that two reversible inhibitors of NEP phosphoramidon and carboxyphenylethyl-Phe-β-Ala (77) inhibit cell growth at nanomolar to micromolar concentrations (FIGS. 1 and 2).

NEP Inhibitors as Anti-Cancer Agents

The present inventors have surprisingly discovered that reversible NEP inhibitors exhibit an inhibitory effect on the growth of CALLA positive leukemia cells. The inventors therefore propose that inactivation of NEP (CALLA) by irreversible inhibitors in the present invention have particular potential as chemotherapeutic agents for acute lymphoblastic leukemia and other CALLA positive tumors. In addition such inhibitors would provide an excellent tool for studies on the involvement of the enzyme in B-cell development and differentiation.

The inventors propose that the following cell lines may be used to assess the effects of the newly synthesized neutral endopeptidase inhibitors on cell growth and viability:

TABLE II

| Cell Line | Characteristics | Reference |
|---|---|---|
| Nalm-6 | CALLA+ human leukemic cell line | 75 |
| Nall-1 | CALLA+ human leukemic cell line | 76 |
| SMS-SB | CALLA− human leukemic cell line | 2 |

TABLE II-continued

| Cell Line | Characteristics | Reference |
|---|---|---|
| TE671 | CALLA+ medulloblastoma cell line | 16 |
| HP 599 | CALLA− glioma | — |
| WI26var | CALLA+ lung cell (SV40 transformed) | 17 |
| Caki (HTB46) | CALLA+ human renal carcinoma cell line | 73 |

These six cell lines are representative of different types of CALLA+ cell lines and control cells. The two leukemic cell lines Nalm-6 and Nall-1 represent the CALLA+ lymphoblastic leukemias while the SMS-SB cell line is an appropriate control for these cell lines since it is also a lymphoblastic leukemia derived cell line but at a more differentiated state and without neutral endopeptidase (CALLA) activity. This cell line should be refractory to effects of the neutral endopeptidase inhibitors.

Assessment of NEP Inhibitors

The efficacy of endopeptidase inhibitors may be assessed by determining cell numbers and the percent of viable cells (e.g., assessed by trypan blue exclusion) as a function of time in culture in the presence and absence of the endopeptidase inhibitors. In addition the level of neutral endopeptidase activity will be measured and correlated with these parameters. Since the enzyme is on the cell surface its activity can be measured by simply adding substrate to the cell culture. The kinetics of inactivation of purified enzyme can also be assessed. A graphical analysis of the inactivation constant (kobs) versus the inhibitor concentration can be plotted. If the inhibitor binds to the active site of the enzyme this graph should be hyperbolic. The data can then be analyzed in a double reciprocal plot of 1/kobs versus 1/[Inhibitor]. This should yield a straight line from which the dissociation constant for the inhibitor (Ki) and the maximal rate of inactivation k(inact) can be obtained. In addition substrates may be used to protect the enzyme from inactivation by the inhibitor to demonstrate that the inhibitor binds to the active site. This type of analysis has previously been conducted to characterize the reaction of both phenylglyoxal and N-bromoacetyl-D-Leu-Gly with the enzyme.

ASSAY FOR NEUTRAL ENDOPEPTIDASE ACTIVITY

NEP: glutaryl-Ala-Ala-Phe-MNA →glutaryl-Ala-Ala + Phe-MNA Aminopeptidase: Phe-MNA →Phe + MNA MNA =4-methoxy-2-naphthylamine The effect of the inhibitor on total neutral endopeptidase protein may be studied by performing quantitative Western Blot analyses. Cells may be collected, pelleted by centrifugation, and resuspended in boiling SDS containing 1% mercaptoethanol. Various amounts of the enzyme are then applied to nitrocellulose paper with a "dot-blot" apparatus. The enzyme may be visualized with an anti-rat kidney neutral endopeptidase antiserum, which reacts equally well with the rat and human enzymes, and iodinated goat anti-human IgG as the secondary antibody. Purified rat kidney enzyme may be used as a standard. A comparison of the enzyme levels in control versus treated cells will determine whether inactivation of the enzyme leads to either an induction of its synthesis or a modulation in which the inactive enzyme is internalized and degraded.

Those inhibitors that appear to affect cell numbers, cell viability, or both may be examined in more detail by measuring the effect of the inhibitor on DNA synthesis using tritiated thymidine. Such measurements, coupled with the analysis of the levels of the endopeptidase itself, may even end in elucidating the mechanisms by which these inhibitors affect CALLA+ cells.

A further extension of these studies includes testing the most promising irreversible NEP inhibitors in an animal system using severe combined immunodeficiency mice (SCID mice) as recipients for Nalm-6 and Nall-1 cells. Both Nall-1 and Nalm-6 cells as well as other human lymphomas and leukemias can be grown in the SCID mouse. The kinetics of growth have shown that growth is related to the number of injected cells. These leukemic cells grow as kidney nodules, as well as grow in the liver and bone marrow and eventually cause hind leg paralysis and death. The viability of the NEP inhibitor treated and control Nalm-6 and Nall-1 cells after injection into the SCID mice may be assessed by sacrificing the animals at various times, removing the kidney and liver, and determining the number of Nalm-6 or Nall-1 cells by immunofluorescence. A monoclonal antibody (e.g., J5) which is specific for human NEP (CALLA) may be employed for this purpose. These studies will thus provide an index as to the ability of the irreversible NEP inhibitors to react with the enzyme on CALLA+ leukemic cells and to prevent their growth in vivo.

Exemplary Studies Employing NEP Inhibitors

When the reversible inhibitors phosphoramidon and carboxyphenylethyl-Phe-$\beta$-Ala were added at nanomolar to micromolar concentrations to CALLA+ leukemia cell lines Nalm-6 and Nall-1, cell growth was inhibited. Nalm-6 and Nall-1 are leukemic cell lines generally representative of CALLA+ lymphoblastic leukemias. FIG. 1 sets fourth studies wherein NEP inhibitors phosphoramidon (1 $\mu$M) and carboxyphenylethyl-Phe-$\beta$-Ala (20 $\mu$M) were added, in separate studies, to Nalm-6, A2/3 and J558 cells, plated in quadruplicate at a density of 100,000 cells/ml in 24 well microliter plates. The number of viable cells was determined daily. In FIG. 2, the NEP inhibitors phosphoramidon (PA;10 nM) and carboxyphenylethyl-Phe-$\beta$-Ala (10 $\mu$M) were added to Nall-1 and, in a separate experiment, to SMS-SB cells plated at a density of 200,000 cells/ml. The inhibitors were added either once on Day 0 as a bolus (closed circle and square) or daily (open circle or triangle). The number of viable cells was determined daily.

Figure 3:
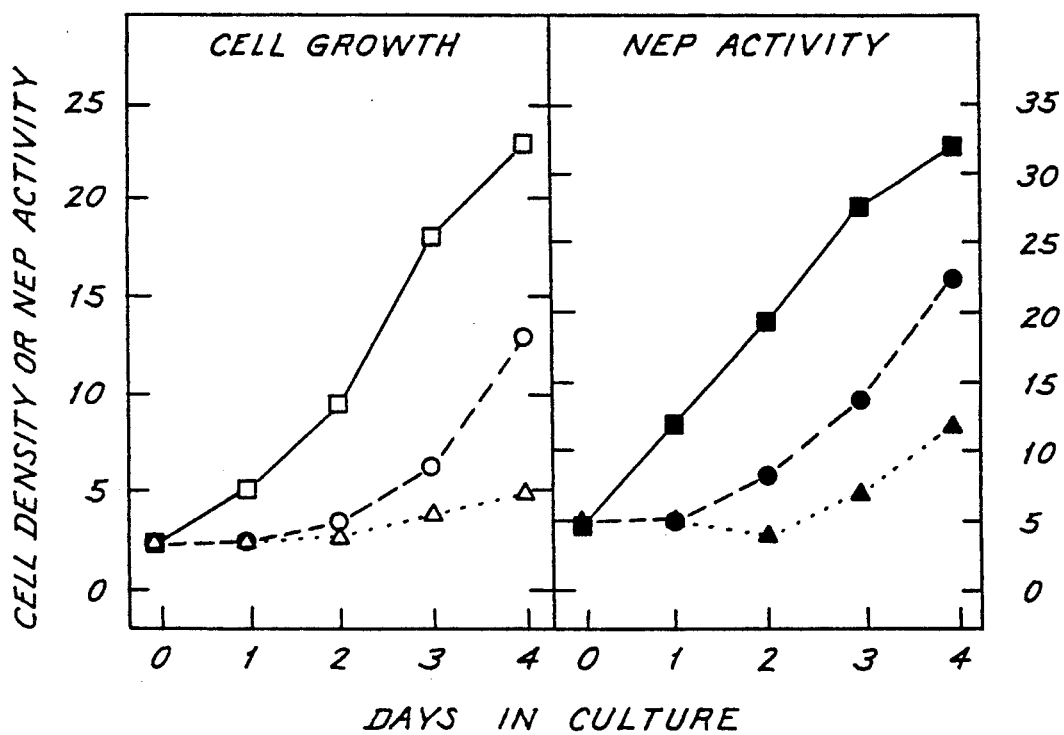
FIG. 3—Correlation of Cell Growth with NEP Activity. Nalm-6 cells were treated with 10 nM phosphoramidon added either as a bolus (circles) or daily (triangles). Cells were initially plated at 200,000 cells/ml. Control cells without added inhibitor are shown as squares. Aliquots were taken daily for determining cell density. To the remainder of the sample was added glutaryl-Ala-Ala-Phe-MNA and NEP activity determined.

The inhibition of cell growth by these NEP specific inhibitors appeared somewhat transient and correlated with the recovery of NEP activity. FIG. 3 shows a study wherein Nalm-6 cells were treated with 10 nM phosphoramidon added either as a bolus (circles) or daily (triangles). Control cells without added inhibitor are shown as squares. Cells were initially plated at a density of 200,000 cells/ml. Aliquots were taken daily for determining cell density. To the remainder of the sample was added glutaryl-Ala-Ala-Phe-MNA and NEP activity was determined.

The NEP inhibitors are stable in media in the presence of Nalm-6 cells. Thus, a loss of inhibitor cannot account for the reversal of growth inhibition. The transient nature of the inhibition of cell growth is believed to result from the incomplete inhibition of NEP activity by the reversible inhibitors. At the concentration for inhibitors tested, there is residual NEP activity at the level of 2-5%. It is believed that this low level of activity is sufficient to produce a metabolite which permits cell growth, albeit at a rather slow rate. Once a sufficient concentration of this metabolite (peptide) is formed, cells commence to grow. There is a dose dependent relationship between the concentration of inhibitor employed and the length of time before cells resume growth.

The use of higher inhibitor concentrations gives a more prolonged inhibition of cell growth such that at 10 μM phosphoramidon growth is inhibited during the entire course of the experiment. At very high inhibitor concentrations, other peptidases can be affected by these inhibitors. Therefore, studies were conducted with the lower inhibitor concentrations in order to maintain specificity.

It is noted that there might be other factors which induce or suppress NEP expression in leukemic cells. Since CALLA/NEP appears to be a reliable marker for common acute lymphoblastic leukemia during the full course of this disease, it would appear that this enzyme is not modulated in vivo on the CALLA+ leukemic cells. The inhibitors used in these studies are not believed to affect the level of NEP expression. The NEP activity of intact cells in the presence of the inhibitors has been measured during the course of experiments similar to those shown in FIG. 1. Although NEP activity d to be inhibited 92-95%, the NEP activity returned to that of untreated cells when the inhibitor was removed by changing the media. This result indicates that the amount of cell surface NEP neither increased or decreased in the presence of the inhibitor.

A control cell line A$ (1), (which is a transfected J558 cell line containing active NEP) and the J558 parental cell are unaffected by these inhibitors (FIG. 1). This result is believed to indicate that simply inhibiting NEP activity per se is insufficient to inhibit cell growth. Since J558 does not normally contain NEP, the enzyme has no function in the A$ transfectant. Thus, inhibiting NEP activity would predictably have no effect. In contrast, NEP is a normal constituent of Nalm-6 cells and inhibition of the enzyme on Nalm-6 cells inhibits growth presumably by blocking the formation of an NEP derived metabolite required for cell growth.

Figure 4A:
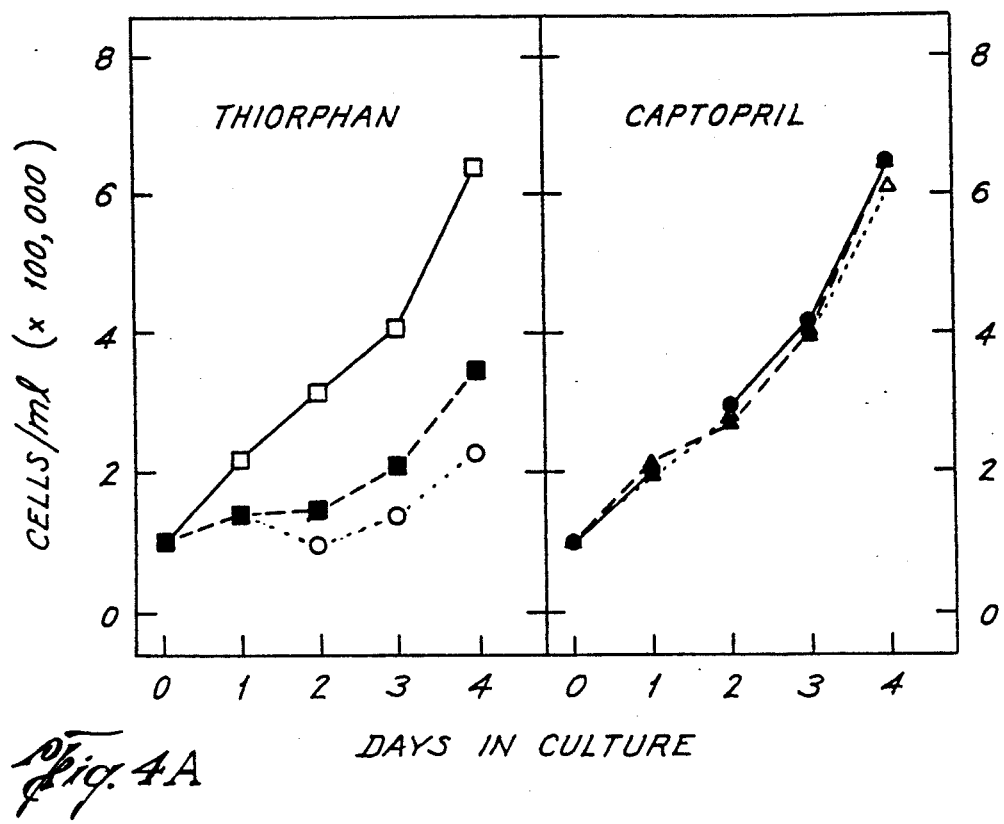
FIG. 4—Effect of Thiorphan and Captopril on the Growth of Nalm-6 (CALLA+) and SMS (CALLA−) Leukemic Cell Lines. The NEP inhibitor thiorphan (10 $\mu M$) and the structurally related compound captopril 10 $\mu M$ were added to cells (open circles and open triangles=daily addition; closed squares and closed triangles=bolus addition). Cells counts were conducted daily.
Figure 4B:
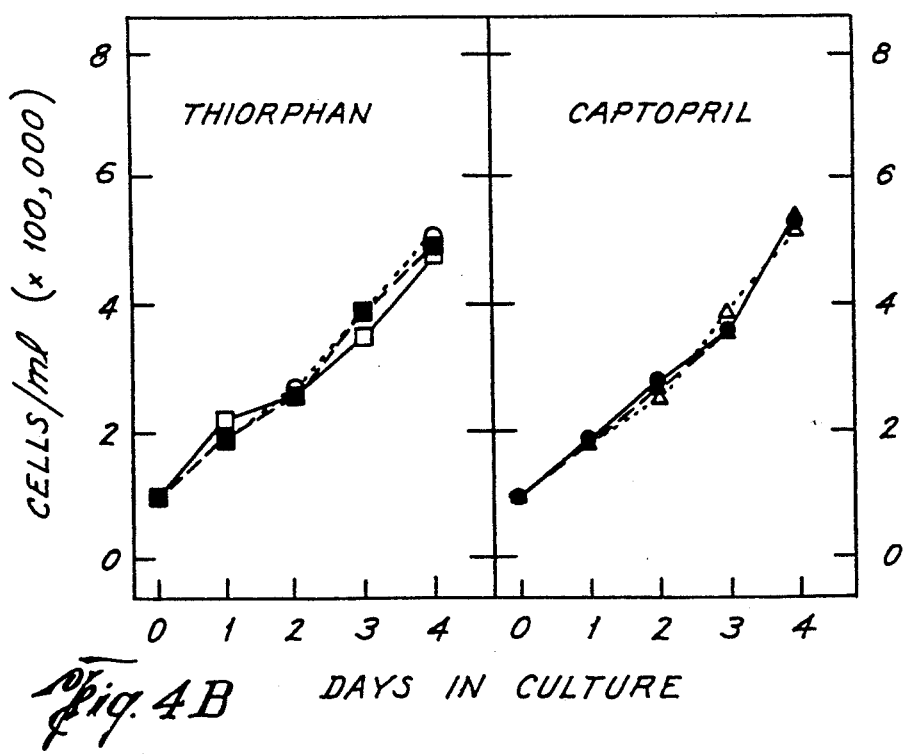

In addition, a CALLA− leukemic cell SMS-SB (2) is also unaffected by these inhibitors, demonstrating that these inhibitors are not simply toxic to leukemic cells, but only effective on leukemic cells which express NEP (FIG. 2). A more dramatic effect on the apparent inhibition of cell growth of the leukemic cell lines is seen when low concentrations of NEP inhibitors are added daily, an effect which can be explained, at least in part, by the increase in inhibitor concentration. In addition, a myoblast cell line, L3, which contains NEP on its cell surface, is unaffected by phosphoramidon and proceeds normally in the formation of myotubules. Additional evidence for the specificity of the effect of NEP inhibitors on the growth of CALLA+ leukemic cells is shown in FIG. 4. The NEP inhibitor thiorphan (HS—CH$_2$—CH(CH$_2$—φ)—CO—Gly, ref. 31) and the structurally related compound captopril (HS—CH$_2$—CH(CH$_3$)—CO—Pro, ref. 19) were added to cells (open circles and open triangles=daily addition; closed squares and closed triangles=bolus addition). Cell counts were conducted daily. In this study, it is shown that another NEP inhibitor, thiorphan inhibits the growth of Nalm-6 cells, while a structurally related compound, captopril, a potent angiotensin converting enzyme inhibitor, is without effect. On the other hand, neither thiorphan nor captopril affect the growth of the CALLA− SMS leukemic cell line (FIG. 4).

To account for the effects of reversible NEP inhibitors on cell growth, it is proposed that CALLA/NEP may act on a substrate precursor to generate a product that is a low molecular weight growth factor. In that NEP is a known peptidase, both product and substrate are likely to be peptides. Moreover, the precursor is likely secreted by the cells themselves rather than being present in the added serum. Under this theory, cell growth is suppressed unless a sufficient concentration of the growth factor can accumulate. Thus, residual CALLA activity explains the transient effect that reversible inhibitors have on cell growth.

Figure 5A:
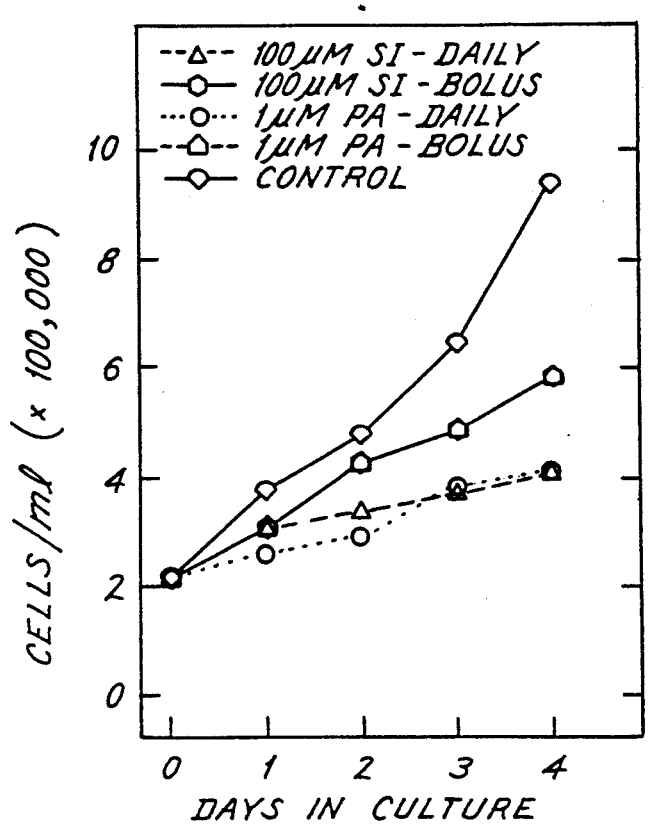
FIG. 5—The Effect of NEP Inhibitors on Nalm-6 Cells Grown in Fresh or Conditioned Media. Nalm-6 cells were grown in fresh media or a 50—50 mixture of fresh media and media taken from a five-day culture. The pH of the conditioned media was adjusted to that of the fresh media. Cell counts were performed daily.
Figure 5B:
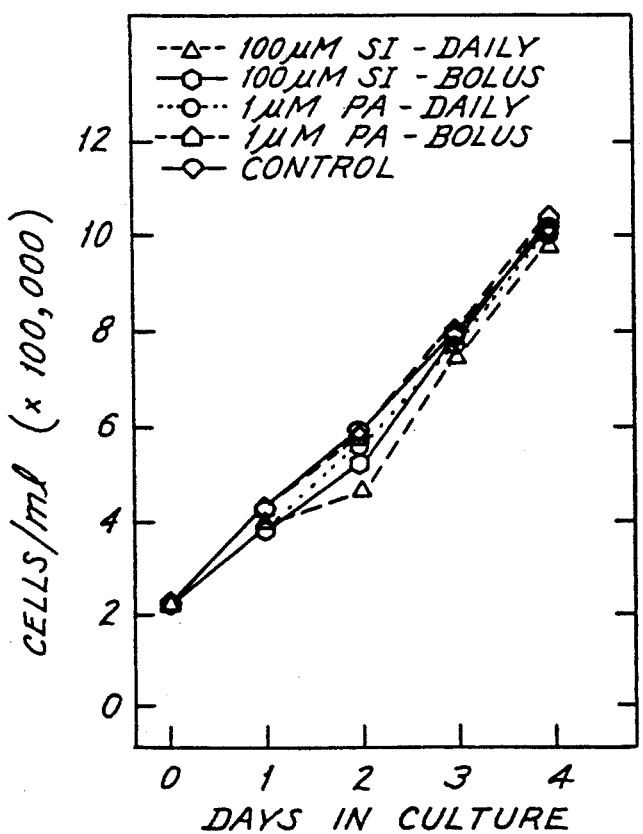

FIG. 5 shows a study wherein Nalm-6 cells were grown in a mixture of fresh and conditioned media taken from a five-day culture in the presence of the high affinity reversible inhibitors phosphoramidon or carboxyphenylethyl-Phe-β-Ala. In conditioned media, the cells grow even though assays showed that enzyme activity was just as effectively inhibited in the conditioned media as in the fresh media. However, when the conditioned media was dialyzed against fresh media (dialysis tubing with a molecular weight cut-off of 14,000) cell growth was once again inhibited by phosphoramidon.

These results are consistent with a hypothesis that NEP generates a growth factor rather than removes an inhibitor. In the latter case, dialysis would have been inconsequential since removal of an inhibitor by dialysis would likely not reintroduce a dependence of cell growth on NEP activity. Furthermore, the fact that this putative growth factor is dialyzable is in keeping with the known specificity of NEP in which certain low molecular peptides are substrates for the enzyme. The largest reported substrate for the enzyme is the 30 amino acid β chain of insulin. It should be noted that NEP need only be one of several enzymes involved in generating this putative growth factor. The growth factor could be derived from a large precursor partially processed by other peptidases. In summary, it is postulated that, as a known peptidase, NEP generates a low molecular weight peptide product which is found in the conditioned media and is required for growth of CALLA+ cells.

From these results, the inventors propose a specific physiological function for NEP on leukemic cells, related to cell growth. This function may not be a general function of NEP on all cell types, and is in keeping with the concept that this enzyme serves various different roles.

NEP/CALLA's catalytic properties indicate that it will also be susceptible to irreversible inhibitors. Based on NEP's putative mechanism of action and NEP's apparent role in cell growth, it is fully expected that specific irreversible inhibitors will sufficiently eliminate residual NEP activity to effectively suppress cell growth in acute lymphoblastic leukemia and other CALLA+ tumors. It is further anticipated that irreversible inhibitors may even produce cell death in that the needed growth factor will not be processed.

It is contemplated that at least two types of irreversible inhibitors may be employable to completely inhibit NEP. A first type are affinity labels based on bromoacetyl-D-Leu-Gly (BADLG). This class of irreversible inhibitor contains a chemically reactive functional group, but gains its specificity by its affinity for the target enzyme. In the second group are mechanism-based inhibitors which are unreactive substrate analogs. These analogs, when bound to the enzyme, are transformed into a reactive molecule which reacts with an active site residue by the reaction mechanism of the enzyme, destroying the enzymes catalytic function.

Histidine and glutamate are nucleophilic residues known to be present at the active site of NEP which appear to play a role in catalysis. (3-5) Both histidine and glutamate can serve as potential targets for a mechanism based inhibitor. Glutamate presumably acts as a proton shuttle in a manner similar to that of Glu 143 in thermolysin (6) and glu 270 in carboxypeptidase A. (7)

Affinity labels for thermolysin and carboxypeptidases A and B are also expected to react with glutamic acid residues. (8-10) A major difference between the mammalian and bacterial enzyme is that the mammalian enzyme contains an active site arginine residue involved in binding substrates at its C- terminal carboxylate.

The following description of irreversible inhibitors is intended to provide examples of certain embodiments of the present invention; it is not an exhaustive list of irreversible inhibitors. As those skilled in the art will recognize, the described invention can be modified to achieve the same or similar results, and still be within the theme of the invention presented by the inventors.

BADLG

Figure 6:
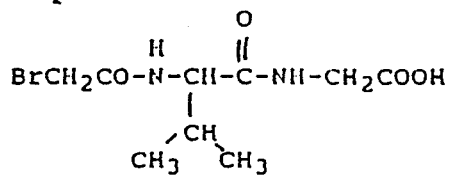
Figure 6:
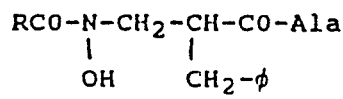
Figure 6:
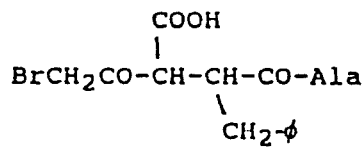
Figure 6:
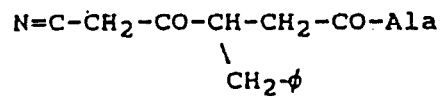
Figure 6:
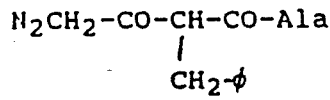
Figure 6:
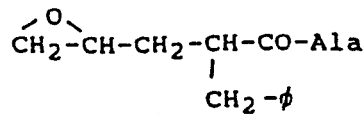

BADLG (FIG. 6, Compound I) is an affinity label of NEP, which reacts with a single histidine in the enzyme. The involvement of this and perhaps a second histidine in catalysis came from kinetic studies using N-acyl dipeptides as substrates and inhibitors. Based on this study, N-bromoacetyl-D-Leu-Gly was synthesized as the first active site directed irreversible inhibitor of the enzyme. This compound acts as a competitive inhibitor ($K_i = 5$ mM), as well as an irreversible inhibitor with 1 mol incorporated per mol of enzyme. This compound binds to the active site of NEP and the bromoacetyl moiety irreversibly reacts with an active site histidine residue.

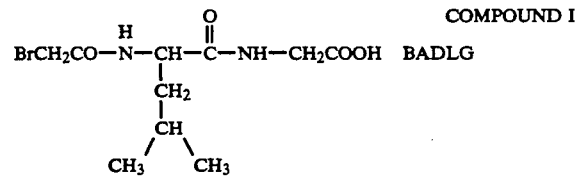

COMPOUND I

BADLG exhibits a relatively weak affinity ($K_i = 5$ mM) for NEP which is due to the presence of a glycine residue in the carboxyl terminal position (S'2 site) and of an amino acid in the D configuration adjacent to it in the S'1 site. It is contemplated that the binding affinity of BADLG can be increased through various modifications. One exemplary modification substitutes an alanine or beta-alanine residue for the glycine residue in BADLG. Studies have shown that neutral amino acids are optimal for the S'2 binding subsite (11). Moreover, the use of alanine or beta-alanine avoids the potential problem of the inhibitor binding in a reversed or "retro" fashion rather than in a productive manner. The binding in a reverse or "retro" mode would place the reactive groups in the wrong place for reaction with the enzyme residues. "Retro" binding has been observed in thermolysin with amino acids containing side chains larger than a methyl group, but this does not appear to happen when small neutral amino acids such as alanine or beta-alanine are used.

Another modification substitutes D-Val and D-Ile for D-Leu in the parent compound bromoacetyl-D-Leu-Gly or, more preferably, the alanine or beta-alanine derivative. Preliminary studies have shown that the compound bromoacetyl-D-Phe-Ala is not an affinity label of NEP presumably because D-phenylalanine is more sterically constrained than leucine and is not able to adopt a conformation which places the bromoacetyl group in proximity to a nucleophilic residue. Using D-Val and D-Ile should produce sufficient hydrophobic interactions while at the same time permit enough flexibility for the side chain to adopt a favorable conformation when bound to the enzyme.

Other possible substitutions include the introduction of hydrophobic amino acids preferably in the L-configuration, rendered inactive as substrates by modification in the alpha nitrogen. Examples of these amino acids would be N-methyl and N-hydroxy leucine or phenylalanine to give the final compounds bromoacetyl-(N-methyl)Leu(or Phe)-Ala and bromoacetyl-(N-hydroxy)Leu(or PHE)-Ala. The hydroxyl, together with the adjacent carbonyl on the bromoacetyl group, can act as a bidentate ligand in coordinating the nearby active site zinc. This should greatly increase the affinity of the compound for the enzyme.

Similar bidentate compounds which contain phenylalanine analogs have been synthesized as reversible inhibitors of NEP by Roques and colleagues (12, 13). Several of these compounds exhibited Ki values in the low nanomolar range. The most potent of these compounds contains a methylene spacer between the alpha carbon of the hydrophobic residue and the hydroxylated nitrogen of the bidentate ligand. An example is Compound IIa, shown below.

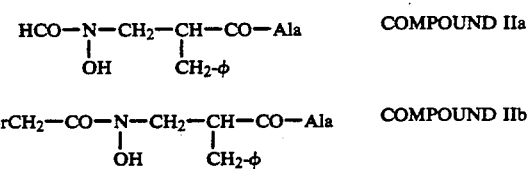

Modifying this compound by substituting a brominated carbon for the terminal hydrogen, as in Compound IIb, should yield a compound of high affinity which would place the bromoacetyl group in a position to react with nucleophilic residues at NEP's active site. It is also expected that the leucine analog of this compound, (substitute an isobutyl group for the benzyl group), should yield a more flexible structure which could more readily adopt a slightly strained conformation. Such strain might be required to permit interaction with the active site zinc and at the same time place the bromoacetyl group in a vulnerable position near active site nucleophilic residues.

Another contemplated affinity label is to inactivate N-acyl substrates such as bromoacetyl-L-Phe-L-Ala by replacing the phenylalanine nitrogen with a methylene carbon. A variation is to add a chelating ligand to the parent compound. For example, in Compound III, a carboxymethyl group is substituted for the nitrogen bonded to the bromoacetyl carboxyl.

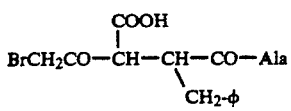  COMPOUND III

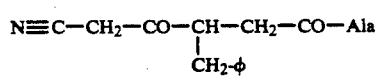  COMPOUND IV

This compound is expected to offer an altered stereochemistry of the bromoketone in the active site and could facilitate reaction with residues which were not in a position to react with the parent compound BADLG. It is proposed that placing bulky substituents at the methylene carbon of the carboxymethyl group will yield a compound with an even higher affinity for NEP. These substituents should bind to the S1 subsite and enhance the affinity of Compound III for NEP.

Mechanism based inhibitors, also known as "suicide substrates," are designed to take advantage of the enzyme's catalytic mechanism, or at least a fortuitous reaction catalyzed by the enzyme. The enzyme activates a latent functional group on the inhibitor which subsequently reacts with an active site residue and inactivates the enzyme. (14)

As previously mentioned, two nucleophilic residues, histidine and glutamate, are known to be present at NEP's active site and apparently play a role in catalysis. The glutamate presumably acts as a proton shuttle in a manner similar to that of glu 143 in thermolysin (6) and glu 270 in carboxypeptidase A (7). Affinity labels for thermolysin, and carboxypeptidases A and B appear to react with glutamic acid residues. (8-10) The second residue known to be present at the active site, histidine, (5,18) also apparently may serve as a target for a suicide inhibitor.

Recently, a mechanism based inhibitor of carboxypeptidase A has been prepared (15). Both carboxypeptidase A and angiotensin converting enzyme are known to catalyze proton abstraction (and deuterium exchange) on substrate analogs which contain a methylene carbon instead of nitrogen at the scissile bond. (20,21) This reaction is no doubt catalyzed by an active site base which normally promotes water attack on the scissile peptide bond during substrate hydrolysis. Since it is believed that NEP utilizes essentially the same reaction mechanism as carboxy-peptidase A and angiotensin converting enzyme, one would also expect NEP to also be capable of catalyzing proton abstraction. Thus, acetylene or nitrile derivatives, which form highly reactive allenes or ketenimines upon abstraction of the neighboring methylene hydrogen, are expected to be effective suicide substrates to NEP as well as other metallopeptidases.

As in the case of the affinity labels described previously, the mechanism based inhibitors could contain either leucine or phenylalanine analogs in the S'1 position and alanine or betaphenylalanine alanine in the S'2 position. Compound IV is an example of such a compound with a phenylalanine analog in the S'1 site and alanine in the S'2 site.

Another "latent" reactive group to insert into a substrate analog would be the diazoketone group. Diazoketones are relatively inert under mildly basic conditions, but become highly reactive when protonated. Diazoketone containing inhibitors of other enzymes, such as proline endopeptidase, have proved to be relatively nontoxic to cultured cells while still maintaining their inhibitory capacity (22). Compound V, shown below, would place the diazoketone group directly into the "beehive" of NEP active site residues participating in catalysis.

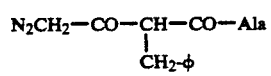  COMPOUND V

Since the enzyme must certainly contain an active site general acid to protonate the leaving amine during catalysis, this general acid could be envisioned to protonate the diazoketone group, rendering it highly reactive towards a nearby enzyme nucleophile. A similar diazoketone is obtained as an intermediate in the synthesis of Compound III noted above. Another functional group which is relatively inert but becomes highly reactive when protonated is the epoxide. Compound VI is an example of a substrate analog containing an appropriately positioned epoxide group, which upon protonation by the enzyme should become highly reactive toward nucleophilic residues in the enzyme.

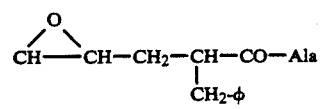  COMPOUND VI

SYNTHESIS OF INHIBITORS

All of the above-described inhibitors can be synthesized by standard organic synthetic procedures. For the synthesis of bromoacetylated dipeptides, including N-methylated and N-hydroxylated dipeptides, bromoacetyl bromide is added slowly to a mildly alkaline solution of the dipeptide, followed by acidification and extraction of the bromoacetylated dipeptide with ethyl acetate. The N-hydroxylated amino acids are prepared by the method of Cook and Slater (23). This method uses hydroxylamine to displace bromine from α-bromocarboxylic acids.

Compound IIb is prepared by a modifying the procedure of Fournie-Zaluski et al (24) as noted in scheme 1, below. In this procedure, 0-benzylhydroxylamine is added to benzylacrylic acid. The product is acylated with bromoacetyl bromide by the procedure of Fournie-Zaluski et al. (24) followed by the coupling of alanine benzyl ester to the acylated product with dicyclohexylcarbodiimide. The final product is obtained by catalytic hydrogenation to remove the benzyl protecting groups.

SCHEME 1:

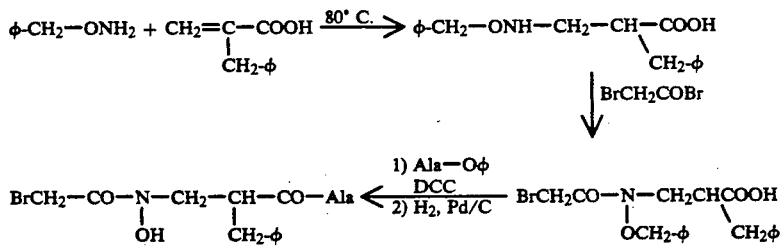

Compound III is prepared by malonic ester displacement of the bromine from 2-bromo-3-phenylpropanoic acid, Scheme 2. The resulting product is then coupled to alanine benzyl ester using dicyclohexylcarbodiimide, esterification by diethylamine in dimethylformamide. Other derivatives of compound IV can be made by the use of different substituents on the succinic anhydride starting material.

SCHEME 3:

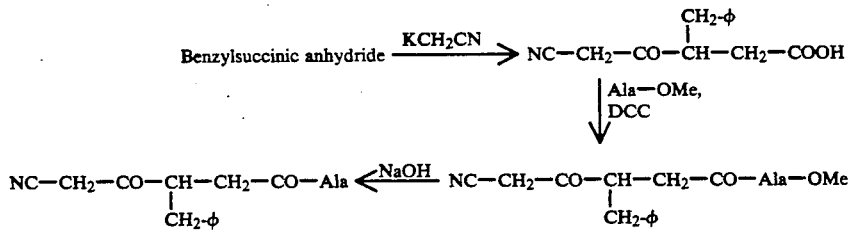

followed by the saponification of one of the malonic esters by adding one equivalent of base. A diazoketone is then generated from the liberated acid using diazomethane and a mixed anhydride activation procedure (25). The second malonic ester is then saponified, the diazoketone transformed into the bromoketone under anhydrous conditions in HBr/diethyl ether. The final step is catalytic hydrogenation to remove the benzyl protecting group.

The diazoketone analog of Phe-Ala (Compound V) is synthesized by adding alanine methyl ester to benzyl malonate monobenzyl ester using dicyclohexylcarbodiimide. The benzyl ester is then removed and the intermediate transformed to the diazoketone as described above for Compound III. The final product is obtained upon removal of the methyl ester by saponification since diazoketones are stable to alkali.

The epoxide analog of Phe-Ala (Compound IV) is

SCHEME 2:

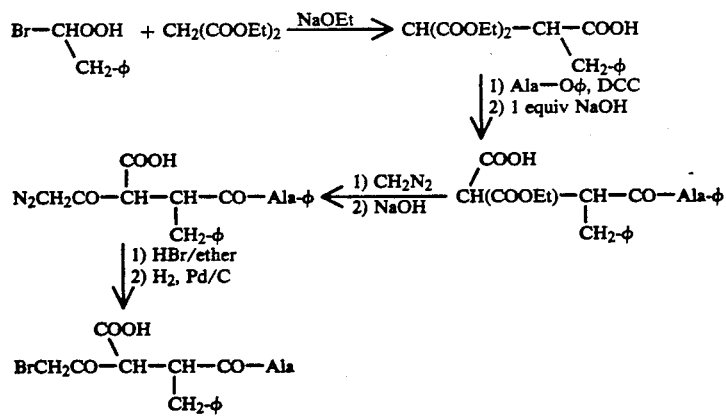

The nitrile analog of Phe-Ala (Compound IV) will be synthesized by adding the potassium salt of acetonitrile to benzylsuccinic anhydride, followed by coupling of alanine methyl ester to the liberated acid and removal of the ester by saponification, Scheme 3. Alternatively, the 9-fluorenylmethyl ester could be used with gentler de- synthesized by attack of diethylbenzylmalonate (via a malonic ester addition) on allyl bromide, followed by de-esterification by saponification and removal of a carboxyl group by heating. Peroxide is then added to form the epoxide. Alanine is added as described in Scheme 4.

SCHEME 4:

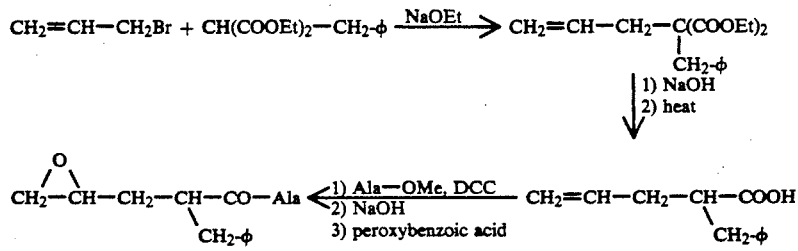

The purity and/or identity of all synthetic compounds is ascertained by thin layer chromatography, HPLC, mass spectrometry, and elemental analysis.

It is believed that the compounds of the present invention will not tend to be particularly toxic when administered to humans in that reversible NEP inhibitors have not demonstrated toxic side effects when administered to animals. In terms of treatment protocols, it should be appreciated that the dosage to be administered will depend on several factors, including the particular analog that is administered, the route administered, the condition of the particular patient, etc. In that most of these agents have peptidyl portions, it will generally be desirable to administer the agents i.v., but administration by other routes is contemplated where appropriate. Generally speaking, one will desire to administer an amount of the agent that is effective to achieve a serum level commensurate with the concentrations found to be effective in vitro. Thus, where an agent is found to demonstrate in vitro activity at, e.g., 10 $\mu$M, one will desire to administer an amount of the drug that is effective to provide about a 10 $\mu$M concentration in vivo. Determination of these parameters are well within the skill of the art.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The references listed below are incorporated herein by reference to the extent that they supplement, explain, provide a background for or teach methodology, techniques and/or compositions employed herein.

1. Shipp, M. A., Vijayaraghavav, J., Schmidt, E. V., Masteller, E. L., D'Adamio, L., Hersh, L. B. & Reinherz, E. (1989) Proc. Nat. Acad. Sci. USA 89, 297.
2. Smith, R. G., Dev, V. G. and Shannon, W. A. (1981) J. Immunol. 126, 596.
3. Devault, A., Nault, C., Zollinger, M., Fournie-Zaluski, M. C., Roques, B. P., Crine, P. and Boileau, G. (1988) J. Biol. Chem. 263, 4033.
4. Bateman, R. C., Jr., Jackson, D., Slaughter, C. A., Unnilter, S., Chai, Y. G., Moomaw, C., and Hersh, L. B. (1987) J Biol Chem 262, 6151-6157.
5. Beaumont, A. and Roques, B. P. (1986) Biochem. Biophys. Res. Comm. 138, 733
6. Holden, H. M. and Matthews, B. W. (1988) J. Biol. Chem. 263, 3265.
7. Lipscomb, W. N., Hartsuck, J. A., Reeke, G. N., Jr., Quiocho, F. A., Bethge, P. H., Ludwig, M. L., Steitz, T. A., Muirhead, H. and Coppola, J. C. (1968) Brookhaven Symp. Biol. 21, 24.
8. Hass, G. M. and Neurath, H. (1971) Biochemistry 10, 3535.
9. Plummer, Jr., T. H. (1971) J. Biol. Chem. 246, 2930.
10. Rasnick, D. and Powers, J. C. (1978) Biochemistry 17, 4363.
11. Hersh, L. B. & Morihara, K. (1986) J. Biol. Chem. 261, 6433.
12. Fournie-Zaluski, M. C., Coulaud, A., Bouboutou, R., Chaillet, P. Devin, J., Waksman,G., Costentin, J., and Roques, B. P. (1985) J. Med. Chem. 28, 1158.
13. Hernandez, J. F., Soleihac, J. M. Roques, B. P. and Fournie-Zaluski, M. C. (1988) J. Med. Chem. 31, 1825.
14. Rando, R. R. (1984) Pharm. Rev. 36, 111.
15. Mobashery, S., Ghosh, S. S., Tamura, S. Y., and Kaiser, E. T. (1990) Proc. Natl. Acad. Sci. USA, 87: 578-582.78.
16. McAllister, R. M., Isaacs, H., Rongey, R., Peer, M., Au, W., Soukup, S. W., and Gardner, M. B., (1977) Int. J. Cancer 20, 206.
17. Girardi, A. J., Jensen, F. C., Caprowski, H. (1985) J. Cell Comp. Physiol. 65, 69.
18. Bateman, R. C., Jr., and Hersh, L. B. (1987) Biochemistry 264, 4237.
19. Ondetti, M. A., Rubin, B., and Cushman, D. W. (1977) Science, 196:441-444.
20. Nashed, N. T. and Kaiser, E. T. (1981) J. Amer. Chem. Soc. 103, 3611.
21. Spratt, T. E. and Kaiser, E. T. (1984) J. Amer. Chem. Soc. 106, 6440.
22. Green, G. D. J. and Shaw, E. (1983) Arch. Biochem. Biophys. 25, 331.
23. Cook, A. H. and Slater, C. A. (1956) J. Chem. Soc. 4130.
24. Fournie-Zaluski, M. C., Coulaud, A., Bouboutou, R., Chaillet, Pl, Devin, J., Waksman, G., Costentin, J., and Roques, B. P. (1985) J. Med. Chem. 28, 1158.
25. Green, G. D. J. and Shaw, E. (1983) J. Biol. Chem. 256, 1923.
26. Kerr, M. A. & Kenny, A. J. (1974) Biochem. J. 137, 477.
27. Kerr, M. A. & Kenny, A. J. (1974) Biochem. J. 137, 489.
28. Schwartz, J. C. (1978) Nature, 276, 523.
29. Sullivan, S., Akil, H. & Barchas, J. D. (1978) Commun. Psychopharmacol.2, 525.

30. Schwartz, J. C., Malfroy, B., and DeLaBaume, S. (1981) *Life Sci.* 29, 1715.
31. Roques, B. P., Fournie-Zaluskie, M. C., Soroca, E., Lecomte, J. M., Malfroy, B. P., Llorens, C., & Schwartz, J. C. (1980) *Nature* 288, 286–288.
32. Schwartz, J. C., Costentin, J., Lecomte, J. M. (1985) *Trends Pharmacol. Sci.* 6, 472.
33. Lecompte, J. M., Costentin, J., Vllaiculescu, A., Chaillet, P., Marcais-Callado, H., Llorens-Cortes, C., Leboyer, M and Schwartz, J. C. (1986) *J. Pharmacol. Exp. Ther.* 237, 937.
34. Chipkin, R. E., Berger, J. G., Billard, W., Iorio, L. C., Chapman, R. and Barnett, A., (1988) *J. Pharmacol. Exp. Ther.* 245, 829.
35. O'Connor, P. and Chipkin, R. E. (1984) *Life Sci.* 35, 631.
36. Swerts, J. P., Perdrisot, R., Malfroy, B., and Schwartz, J. C. (1979) *Eur. J. Pharmacol.* 53, 209.
37. Almenoff, J., Wilk, Sl., & Orlowski, M. (1981) *Biochem. Biophys. Res. Commun.* 102, 206.
38. Fulcher, I. S., Matsas, R., Turner, A. J., & Kenny, A. J. (1982) *Biochem. J.* 203, 519.
39. Hersh, L. B. (1982) *Mol. Cell. Biochem.* 47, 35.
40. Llorens, C. and Schwartz, J. C. (1981) *Eur. J. Pharm.* 69, 113.
41. Gee, N. S., Bowes, M. A., Buck, P. and Keney, A. J. (1985) *Biochem. J.* 228, 119.
42. Matsas, R., Fulcher, I. S., Kenny, A. J. & Turner, T. (1983) *Proc. Natl. Acad. Sci. USA* 80, 3111.
43. Olins, G. M., Spear, K. L., Siegel, N. R., Zurcher-Neely, H. A. (1987) *Biochem. Biophy. Acta* 901, 97.
44. Greaves, M. F., Brown, G., Rapson, N. T., & Lister, T. A. (1975) *Clin. Immunol. Immunopathol.* 4, 67.
45. LeBien, T., Hurwitz, R. L. & Kersey, J. H. (1979) *J. Immunol.* 22, 82.
46. Pesando, J. M. Ritz, J., Lazarus, H., Costello, S. B., Sallan, S. E. & Schlossman, S. F. (1979) *Blood* 54, 1240.
47. L., Sen, L., & Casper, J. T. (1977) *J. Immunol.* 118, 309.
48. Ritz, J., Pesando, J.M., Notis-McConarty, J., Lazarus, H., & Cshlossman, S. F. (1980) Nature, 283, 583.
49. Ritz, J., & Schlossman, S. F. (1982) *Blood* 59, 1.
50 Braun, M. p., Martin, P. J., Ledbetter, J. A., & Hansen, J. A. (1983) *Blood* 61, 718.
51. Ritz, J., Nadler, L. M., Bhan, A. K., Notis-McConarty, J., Pesando, J. M. and Schlossman, S. F. (1981) *Blood* 58, 658.
52. Carrel, S., DeTribolet, N., Gross, N. (1982) *Eur. J. Immunol.* 12, 354.
53. Greaves, M. F., Hairi, G., Newman, R. A., Suyherland, D. R., Ritter, M. A., & Ritz, J. (1983) *Blood* 61, 628.
54. Hokland, P., Rosenthal, P., Griffin, J. D., Nadler, L. M., Daley, J., Hokland, M., Schlossman, S. F. & Ritz, J. (1983) *J. Exp. Med.* 157, 114.
55. Hokland, P., Nadler, L. M., Griffin, J. D. & Schlossman, S. F. & Ritz, J. (1984) *Blood* 64, 662.
56. Braun, M. P., P. J., Ledbetter, J. A., & Hansen, J. A. (1983) *Blood* 61, 718.
57. Ritz, J., Takvorian, T., Sallan, S. F., Freedman, A. S., Anderson, K., Coral, F., Schlossman, S. F., & Nadler, L. M. (1987) in Leukocyte Typing III: White Cell Differentiation Antigens, ed. McMichael, A. J. (Oxford U. Press, N.Y.)
58. Ritz, J., Pesando, J. M., Notis-McConarty, J. & Schlossman, S. F. (1980) *J. Immunol.* 125, 1506.
59. Pesando, J. M., Ritz, J., Lazaris, H., Tomaselli, K. J., & Schlossman, S. F. (1981) *J. Immunol.* 125, 1506.
60. Malfroy, B., Schofield, P. R., Kuang, W. J., Seeburg, P. H., Mason, A. J., and Henzel, W. J. (1987) *Biochem. Biophys. Res. Comm.* 144, 59.
61. Devault, A., Lazure, C., Nault, C., Le Moual, H., Siedah, H., Chretein, M., Kahn, P., Powell, J., Mallet, J., Beaumont, A., Roques, B. P., Crine, P. and Boilleau, G. (1987) *EMBO J.* 6,1317.
62. Malfroy, B., Kuang, W. J., Seeburg, P. H., Mason, A. J. and Schoeifled, P. R. (1988) *FEBS Lett.* 229, 206.
63. Shipp, M. A., Richardson, N. E., Sayre, P. H., Brown, N. R., Masteller, E. L., Clayton, L. K., Ritz, J. & Reinherz, E. (1988) *Proc. Nat Acad. Sci. USA* 85, 4819.
64. Letarte, M., Vera, S., Tran, R., Addis, J. B., Onizuka, R. J., Quackenbush, E. J., Jongeneel, C. V., and McInnes, R. R. (1988) *J. Exp. Med.* 168, 247.
65. Rush, R. S. & Hersh, L. B. (1982) *Life Sci.* 31, 445.
66. Gafford, J. T., Skidgel, R., Erdos, E. G. & Hersh, L. B. (1983) *Biochemistry* 22, 3265.
67. Rush, R. S., Mitas, M., Powers, J. C., Tanaka T. and Hersh, L. B. (1984) *Arch. Biochem. Biophys.* 231. 390.
68. Hersh, L. B. (1984) *J. Neurochem.* 43, 487.
69. Almenoff, J. and Orlowski, M. (1984) *J. Neurochem.* 42, 151.
70. Orloski, M., and Wilk, S. (1981) *Biochemistry* 20, 4942.
71. Blumberg, S., Vogel, Z., & Alstein, M. (1981) *Life Sci.* 28, 301.
72. Mumford, R. A., Pierzchala, P. A., Strauss, A. W., & Zimmerman, M. (1981) *Proc. Natl., Acad. USA* 78,6623.
73. Prager, M. D., and Kaner, M. C. (1984) Cancer Lett. 24, 81.
74. Benchetrit, T., Bissery, V., Mornon, J. P., Devault, A., Crine, P. and Roques, B. P. (1988) *Biochemistry* 27, 592–596.
75. Hurwitz, R., Hozier, J., LeBien, T., Minowada, J., Kazimiera, G. P., Kuboniski, I., and Kersey, J. (1979) *Int. J. Cancer* 23, 174.
76. Minowada, J. (i983) Immunol. of Leuk. Cells In Leukemia (F. W. Gunz and E. S. Henderson, ed) IVth edition Crine an Stratton, Publishers, N.Y., p. 119.
77. Mumford, R. A., Zimmerman, M., tenBroeke, J., Taub, D., Joshua, H., Rothrock, J. W., Hirshfield, J. M., Springer, J. P. and Patchett, A. A. (1982) *Biochem. Biophys. Res. Commun.* 109, 1303.

What is claimed is:

1. A method of inhibiting the growth or differentiation of CALLA+ human leukemia cells comprising subjecting such cells to an effective amount of an NEP inhibitor.

2. The method of claim 1, wherein the NEP inhibitor is an irreversible inhibitor.

3. The method of claim 1, wherein the NEP inhibitor is an affinity-label inhibitor.

4. The method of claim 3, wherein the affinity label inhibitor comprises BADLG, or a derivative thereof, wherein alanine or beta-alanine is substituted for glycine.

5. The method of claim 4, wherein the NEP inhibitor comprises BADLG wherein a hydrophobic amino acid is substituted for D-Leu.

6. The method of claim 5, wherein the hydrophobic amino acid comprises D-Val or D-Ile.

7. The method of claim 5, wherein the hydrophobic amino acid is rendered inactive by modification to the alpha-nitrogen.

8. The method of claim 7, wherein the hydrophobic amino acid comprises bromoacetyl-(N-methyl) (Leu or Phe)-Ala, or bromoacetyl-(N-hydroxy)(Leu or Phe)-Ala.

9. The method of claim 1, wherein the NEP inhibitor comprises an NEP inhibitor with the formula:

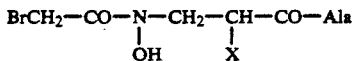

wherein:
X = —CH$_2$—φ, isopropyl or isobutyl,
or a derivative or analog thereof.

10. The method of claim 9, wherein the NEP inhibitor comprises a substitution for the BrCH$_2$ group.

11. The method of claim 1, wherein the NEP inhibitor comprises an inactivated N-acyl substrate analog.

12. The method of claim 11, wherein the inactivated N-acyl substrate has the formula:

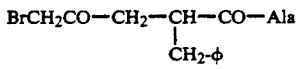

13. The method of claim 11, wherein the inactivated N-acyl substrate contains a chelating ligand.

14. The method of claim 13, wherein the inactivated N-acyl substrate is:

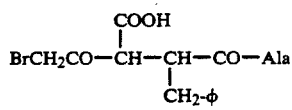

15. The method of claim 1, wherein the NEP inhibitor comprises an acetylene or nitrile substrate analog.

16. The method of claim 15, wherein the NEP inhibitor has the formula:

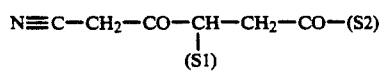

wherein:
S1 = benzyl, isobutyl, or their analogs; and
S2 = Ala, β-Ala, gly or their analogs.

17. The method of claim 16, wherein the NEP inhibitor has the formula:

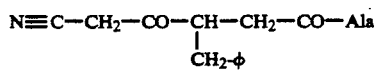

18. The method of claim 1, wherein the NEP inhibitor comprises a diazoketone-containing substrate analog.

19. The method of claim 18, wherein the NEP inhibitor has the chemical formula:

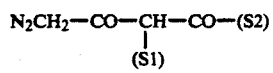

wherein:

S1 = benzyl, isobutyl, or their analogs; and
S2 = Ala, β-Ala, gly or their analogs.

20. The method of claim 18 wherein the NEP inhibitor has the formula:

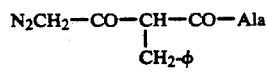

21. The method of claim 18 wherein the NEP inhibitor has the formula:

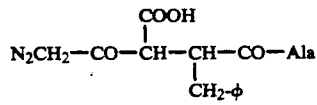

22. The method of claim 1, wherein the inhibitor compound is:

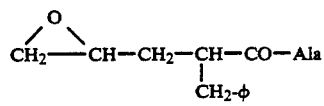

23. An NEP inhibitor comprising BADLG, or a derivative thereof, wherein alanine or beta-alanine is substituted for glycine.

24. The NEP inhibitor of claim 23, wherein a hydrophobic amino acid is substituted for the D-Leu of BADLG.

25. The NEP inhibitor of claim 24, wherein the hydrophobic amino acid comprises D-Val or D-Ile.

26. The NEP inhibitor of claim 24, wherein the hydrophobic amino acid is rendered inactive by modification to the alpha-nitrogen.

27. The NEP inhibitor of claim 26, wherein the hydrophobic amino acid comprises bromoacetyl-(N-methyl) (Leu or Phe)-Ala, or bromoacetyl-(N-hyroxy)(Leu or Phe)-Ala.

28. An NEP inhibitor which comprises the formula:

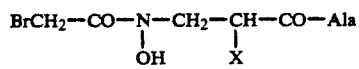

wherein:
X = —CH$_2$—φ, isopropyl or isobutyl,
or a derivative or analog thereof.

29. An NEP inhibitor having the formula:

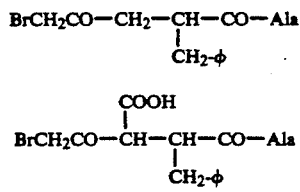

30. An NEP inhibitor having the formula:

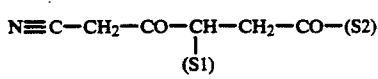

wherein:
S1 = benzyl, isobutyl, or their analogs; and

S2=Ala, β-Ala, gly or their analogs.

31. The NEP inhibitor of claim 30, wherein the NEP inhibitor has the formula:

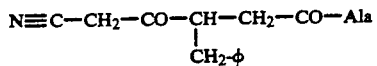

32. An NEP inhibitor having the formula:

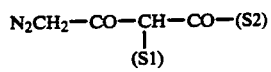

wherein:
S1=benzyl, isobutyl, or their analogs; and
S2=Ala, β-Ala, gly or their analogs.

33. The NEP inhibitor of claim 32 wherein the NEP inhibitor has the formula:

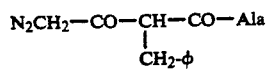

34. The method of claim 32 wherein the NEP inhibitor has the formula:

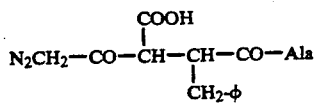

35. An NEP inhibitor having the formula:

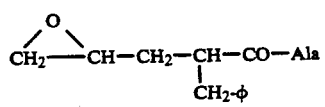

* * * * *

UNITED STATES PATENT AND TRADEMARK OFFICE
CERTIFICATE OF CORRECTION

PATENT NO. : 5,200,426

DATED : April 6, 1993

INVENTOR(S) : Louis B. Hersh and R.C. Bateman, Jr.

It is certified that error appears in the above-identified patent and that said Letters Patent is hereby corrected as shown below:

At column 22, line 55, insert --or--.

Signed and Sealed this

Seventh Day of December, 1993

Attest:

BRUCE LEHMAN

Attesting Officer

Commissioner of Patents and Trademarks